US006304187B1

(12) United States Patent
Pirim (10) Patent No.: US 6,304,187 B1
(45) Date of Patent: Oct. 16, 2001

(54) METHOD AND DEVICE FOR DETECTING DROWSINESS AND PREVENTING A DRIVER OF A MOTOR VEHICLE FROM FALLING ASLEEP

(75) Inventor: Patrick Pirim, Paris (FR)

(73) Assignee: Holding B.E.V. S.A., Luxembourg ( * ) Notice: Subject to any disclaimer, the term of this patent is extended or adjusted under 35 U.S.C. 154(b) by 0 days.

(21) Appl. No.: 09/600,394
(22) PCT Filed: Jul. 22, 1999
(86) PCT No.: PCT/FR99/00060
§ 371 Date: Jan. 26, 2001
§ 102(e) Date: Jan. 26, 2001
(87) PCT Pub. No.: WO99/36894
PCT Pub. Date: Jul. 22, 1999

(30) Foreign Application Priority Data

Jan. 15, 1998 (FR) .................................................. 98 00378

(51) Int. Cl.⁷ .................................................. G08B 23/00
(52) U.S. Cl. .......................... 340/576; 340/575; 340/573; 340/691; 340/693
(58) Field of Search .................................. 340/575, 576, 340/573.1, 573.4, 691, 693

(56) References Cited

U.S. PATENT DOCUMENTS

| 4,259,665 | 3/1981 | Manning ............................... 340/575 |
| 4,485,375 | 11/1984 | Hershberger ......................... 340/576 |
| 4,555,697 | 11/1985 | Thackrey ............................... 340/575 |
| 4,928,090 | 5/1990 | Yoshimi et al. ....................... 340/575 |

(List continued on next page.)

FOREIGN PATENT DOCUMENTS

| 19715519 A1 | 11/1997 | (DE) . |
| 19715519A1 | 11/1997 | (DE) .............................. G08B/21/00 |
| WO 97/01246 | 1/1997 | (WO) .............................. H04N/7/18 |
| WO 98/05002 | 2/1998 | (WO) .............................. G06T/7/20 |

OTHER PUBLICATIONS

Ueno, H. et al.: "Development of Drowsiness Detection System" 1994 Vehicle Navigation & Information Systems Conference Proceedings, pp. 15–20 (1994), XP 000641294.

Ueno, H., et al.: "Development of Drowsiness Detection System", *Proceedings of the Vehicle Navigation and Information Systems Conference*, Yokohama, Aug. 31–Sep. 2, 1994, Aug. 31, 1994, pp. 15–20, XP00064194, Institute of Electrical and Electronics Engineers.

*Primary Examiner*—Jeffery Hofsass
*Assistant Examiner*—Hung Nguyen
(74) *Attorney, Agent, or Firm*—Townsend and Townsend and Crew, LLP (57) ABSTRACT

The invention relates to a method and device using an optoelectronic sensor in combination with an electronic unit arranged inside a motor vehicle. The sensor is adjusted in line with the head of the driver sitting in said motor vehicle at the same time as the inner rear-view mirror, which comprises a one-way mirror behind which the sensor is positioned. After detecting the presence of a driver seated in the motor vehicle they frame first the whole face and then the eyes of the driver in the video signal raser emitted by the sensor aided by the electronic unit and then determine the successive durations of blinking episodes, which are compared with a limit value situated between one duration typical of an awake person and another duration typical of a drowsy person. A signal (transmitted by an alram unit) suitable for waking the driver is triggered when the duration of blinking exeeds the limit.

18 Claims, 6 Drawing Sheets

U.S. PATENT DOCUMENTS

| | | | |
|---|---|---|---|
| 5,195,606 | 3/1993 | Martyniuk | 180/272 |
| 5,353,013 | 10/1994 | Estrada | 340/575 |
| 5,402,109 | 3/1995 | Mannik | 340/575 |
| 5,469,143 | 11/1995 | Cooper | 340/575 |
| 5,682,144 | 10/1997 | Mannik | 340/575 |
| 5,684,461 | 11/1997 | Jones | 340/575 |
| 5,689,241 | 11/1997 | Clarke, Sr. et al. | 340/575 |
| 5,729,619 | * 3/1998 | Puma | 340/576 |
| 5,786,765 | * 7/1998 | Kumakura et al. | 340/576 |
| 5,813,993 | 9/1998 | Kaplan et al. | 600/544 |
| 5,841,354 | 11/1998 | Bae et al. | 340/575 |
| 6,097,295 | * 1/1999 | Griesinger et al. | 340/576 |
| 6,151,065 | * 11/2000 | Steed et al. | 348/148 |

* cited by examiner

METHOD AND DEVICE FOR DETECTING DROWSINESS AND PREVENTING A DRIVER OF A MOTOR VEHICLE FROM FALLING ASLEEP

The present invention relates to a process and device for continuous monitoring of the driver's watchfulness in an automotive vehicle, in order to detect and to prevent any possible sleepiness of the former.

We know that a significant, if not important, proportion of the road accidents are caused by total or partial (dizziness) sleepiness of an automotive vehicle's driver (personal car, utility vehicle, van, lorry) thus resulting in numerous deaths and casualties.

The issue consisting in triggering an alarm, notably a sound alarm, as soon as the driver is falling asleep, in order to wake him/her up, appears of paramount significance from a human as well as economic viewpoint.

To detect a driver's sleepiness, it has been suggested as follows, in an automotive vehicle
  on the one hand, to detect any variation in a driver's controlling the steering wheel when falling asleep and
  on the other, to detect any variation in the vertical movements of a driver's eyelids when falling asleep.

The present invention implements a detection of the second type above mentioned (monitoring the movements of the eyelids) and it is based upon a physiological observation, i.e. the modification in the blinking duration, as well as time intervals between two successive winks, hence the blinking rhythm as a person is switching from a woken condition to dizziness before he/she falls asleep: the duration of a person's wink is in the order of 100 to 200 ms (milliseconds) when he/she is awake and in the order to 500 to 800 ms when he/she is feeling sleepy whereas the time interval between two successive winks, which is more or less constant in woken condition, varies over relatively wide a range in a sleepy condition. It is the variation in the blinking duration which is essentially implemented within the framework of the invention.

The process and the device according to the invention detect the increase in the driver's blinking duration and trigger an alarm, a sound or other, when the said duration exceeds a set threshold, ranging in particular between 200 and 500 ms, for instance equal to 350 ms, whereby this threshold can be modified in relation to the driver's physiology.

In the French patent application n° 96.09420 made on Jul. 26, 1996 and the international patent application (P.C.T.) PCT/FR97/01354 made on Jul. 22, 1997, while stressing the priority of the said French patent application, whereas the inventor of both these applications is also the present invention's inventor, we described a process and a device, operating in real time, for locating and circumscribing a zone in relative motion within a scene, as well as for determining the speed and the displacement direction.

Among the applications contemplated for this process and this device, we described in the said patent applications, the implementation of the said process and device for observing and monitoring a zone consisting of an automotive driver's head, in order to detect and to prevent the driver from falling asleep.

According to this particular application of the process and device of the said patent applications:
  a video signal was produced, significant in real time of the successive pictures of the driver's eyes;
  this video signal was processed in order to, successively and continuously,
    detect, in the pictures of this driver's eyes, the vertical movements of the eyelids significant of their blinking;
    determine the rhythm of these vertical movements and locate the rhythms smaller than a given threshold, corresponding more or less to the blinking rhythm of a driver when fully awake; and
  an alarm was triggered when this threshold was exceeded downwards by the said rhythms, in order to wake up the driver.

The purpose of this invention is to perfect the process and device of the patent applications mentioned above, as regards their application to monitoring an automotive driver, in order to detect his/her possible sleepiness.

The Hiroshi Ueno and Al article, title <<Development of drowsiness detection system>>, published in the Institute of Electrical and Electronics Engineers journal (IEEE) Aug. 31, 1994, pages 15–20, analyses several automotive driver drowsiness detection technics. Specifically, the use of a videocamera associated with a video image treatment calculator is mentioned, with a software realising, on one hand, detection of the driver face, particularly a rectangle including one eye, and, on the other hand, of the rate of the opened eyes and closed eyes durations to determine drowsiness criteria.

Moreover, the published German patent application DE-197 15 519 and the published corresponding French patent application n°2 747 346 describe a device and a process of estimation of the level of the dizziness of an automotive driver with a video camera located by the foot of the vehicle driver and a calculator for the treatment of the image produced by the camera, with a software detecting eyes blinks by the determination of the delay between the start and the end of the blinks. In particular a unit 10 of the calculator realises:
  memorisation of the video image and its treatment in order to determine an area including the driver's eyes;
  the detection of the time interval between the closure of the driver's eyes-lids and their complete opening;and
  a treatment in a memory 11 and a calculation unit 22, in combination with unit 10, in order to calculate a ratio of slow blinks apparition.

Lastly, the published international application WO 97/01246 subject matter is a security system including a video camera arranged in an automotive vehicle interior mirror and a video screen at distance for analysing what is occurring in the vehicle and around it, and what occurred thanks to the recording of the video camera output signal. This is, in fact, a hidden camera (in the rear mirror), in order to escape intruder attention and which observes a wide area including the interior and the environment of the vehicle, the recording allowing a later knowledge of what occurred in this area (page 6, lines 13 to 19), and not a sensor which vision angle is sensibly limited to the driver's face in order to detect his possible sleepiness and waking up him.

It can be seen that those documents (above mentioned articles and applications) are using a genuine video camera and an external calculator, the eye blinks detection in this article and those French and German applications requiring a complex treatment unit while said international application does not solve the sleepiness detection problem, the driver if sleepy being not capable of looking at the video screen neither at the video recording. It can be seen that one can not combined this document to the two preceding documents as they do not belong to the same technical field.

Compared to those documents, the present invention realises a better approach of the driver eyes blinks duration measurement capture; as it allows the use in the vehicle rear mirror of a simple sensor (eventually the sensor of a minute video camera), specially MOS sensor, which is not necessarily in the standard video format;

it realises a movement of the transducer optical axis linked to the rear mirror displacement by the driver in order to direct said axis toward driver's face;

it allows an integrated visual perception, an integrated circuit allowing an immediate detection of the eyes lids movements;

it uses a very simple processor for the treatment of the sensor information;

it allows the integration in an electronic chip of the sensor, its associated electronic circuitry and the calculator, all being arranged in the rear mirror;

it permits the possibility of associate such a chip in the rear mirror with a dashboard processor, the rear mirror being thus an intelligent sleepiness detection device at a moderate cost as it includes, compared to a standard interior rear mirror, simply a chip and a mechanical set for this additional chip orientation.

In those conditions, the object of the invention is first of all a process for continuous monitoring of the driver's watchfulness in an automotive vehicle in order to detect and prevent any sleepiness of the said driver, which consists in producing a video signal, significant in real time of the successive pictures of at least the driver's face;

processing this signal, successively and continuously, to detect in this signal the portion corresponding effectively to the image of the driver's head, determine the value of a parameter in relation to the blinking of the eyelids, with a notable modification when the driver passes from the awake condition to the sleepy condition, on either side of a threshold, and locate in real time when the value of this parameter exceeds this significant threshold of the driver's transition from awake condition to sleepy condition; and triggering, in response to the threshold being exceeded, an alarm capable of waking up the driver;

and which is characterised in that on the one hand, the video signal is produced by using an optoelectronic sensor interconnected with a rear-mirror on the automotive vehicle, dimensioned and arranged to essentially receive the driver's face image when seated and whose optic axis for receiving the light rays is directed towards the driver's head when the rearmirror is oriented correctly;

and on the other, processing the said video signal consists, after detecting the presence of the driver on his/her seat, successively and continuously, in:

detecting, from an analysis of moving pixels between two successive frames of same nature of said video signal, the horizontal movements of the driver, in order to centre the face of the said driver within the successive corresponding frames of the video signal, detecting, from an analysis of moving pixels between two successive frames of same nature of said video signal, the vertical movements in the face, thus centred, of the driver in order to centre his/her eyes, determining, from an basis of an analysis of moving pixels between two successive frames of same nature of said video signal, the successive blinking durations of the eyes, thus centred, of the driver, whereby the said durations make up the said parameter, comparing these successive blinking durations, thus determined, with a threshold significant of the transition from awake condition to sleepy condition of the driver, and triggering, when the blinking durations exceed the said threshold upwards, an alarm capable of waking up the driver.

Advantageously, the said sensor is placed in the casing of the rear mirror behind the glass of the former which consists of a two-way mirror, the reception optic axis of said sensor being symmetrical to and axis oriented in the vertical median plane of said vehicle, related to an orthogonal axis to said two way mirror.

Preferably, the presence of the driver on his/her seat is detected while determining the number of pixels corresponding in the successive frames of the same nature in the video signal for which a significant movement is detected and by comparing this number with the total number of pixels per frame of the video signal, in order to determine whether the ratio between the number of pixels representing a displacement and the total number of pixels per frame exceeds a threshold significant of the transition from the driver's absence on his/her seat to the presence of a driver in his/her seat.

The process may, in preferred embodiments, comprise moreover one or several of the following characteristics:

between the detection phases of horizontal displacements, in order to centre the driver's face, and the detection of vertical displacements, in order to frame the driver's eyes, a wide centring phase of the eyes has been provided while being limited to a portion of the centred face, covering the eyes and their immediate surrounding, by applying the anthropometric ratio between the said portion and the entire face of a person;

simultaneously to the determination phase of the blinking durations, a determination phase of time intervals between two successive winks has been provided and a reinforced alarm should be triggered as soon as those time intervals present an irregularity which exceeds a set threshold;

continuous update of the data regarding at least one of the following parameters: horizontal displacements, vertical displacements, blinking durations, intervals between successive winks, in order to perfect the approximations of the normal values of these parameters for the driver actually present and in awake condition;

the different successive phases of the process are performed using successive computer programmes which would process successive values of the corresponding pixels of the frames of same nature in the video signal obtained from the said sensor.

The object of the present relation is also a device for continuous monitoring of a driver's watchfulness in an automotive vehicle, in order to detect and prevent any sleepiness of the said driver, implementing the process above mentioned and characterised in that it comprises, as a combination:

a) an optoelectronic sensor which, in combination with associated electronic circuitry, prepares, in response to the reception of light rays, a video signal with frames of the same nature, or corresponding, successive frames, whereas the said sensor is interconnected with a vehicle rear mirror and dimensioned and arranged to essentially receive the driver's face image when seated and whose optic axis for receiving the light rays is directed towards the driver's head when the rear mirror is suitably oriented;

b) at least an integrated circuit including means to detect the driver's presence on his/her seat in the vehicle, and to prepare a presence signal;

means, actuated by this presence signal, to detect on the basis of an analysis of mowing pixels between to two successive frames of same nature of said video signal, the horizontal displacements of the said driver, in order to centre his/her face in the corresponding successive frames of same nature in the video signal and to prepare a signal at the end of the face centring;

means, actuated by the said end signal of the face centring, to detect on the basis of an analysis of moving pixels between two successive frames of same nature of the portion of the successive frames of same nature in the said video signal corresponding to the face centring, the vertical displacements in the face, thus centred, of the driver, in order to centre the eyes of the said driver, within the said portion of the frames of this signal and to prepare a face centring end signal of the driver's eyes;

means, actuated by the said eyes centring end signal, to determine on the basis of an analysis of moving pixels between two successive frames of same nature of the portion of the successive frames of same nature in the video signal corresponding to the eyes centring, the successive durations of the driver's blinking;

means to compare these successive blinking durations, thus determined, with a threshold significant of the transition from awake condition to sleepy condition of the driver; and means to trigger, when the blinking durations exceed the said threshold, an alarm capable of waking up the driver.

Advantageously, in the said device, the said sensor is located in the rear mirror casing behind the glass of the former, which is a two-way mirror, said sensor being carried by a first extremity of a first rod crossing, through a trunnion, a clamp carried by the rear mirror casing, inside of it, the second extremity of this rod being freely articulated, with a seam, to the first extremity of a second rod crossing, through a trunnion, the rear mirror casing, while the second extremity of said second rod is fixed to the bodywork of the vehicle above the front windscreen, in order that the said reception optic axis of said sensor being symmetrical to an axis directed in the vertical median plane of said vehicle, related to an axis which is orthogonal to said two way mirror.

Preferably, the said means to detect the presence of the driver on his/her seat and to prepare a presence signal consist of means to determine the number of pixels in the successive frames of same nature in the video signal for which a significant displacement has been detected, means to compare the same number with the total number of pixels per frame of the video signal, in order to determine whether the ratio between the number of pixels corresponding to a displacement and the total number of pixels per frame exceeds a threshold significant of the transition from the driver's absent condition on his/her seat to the presence of a driver on his/her seat.

The device may, in preferred embodiments, comprise moreover one or several of the following means, i.e.:

means, actuated by the said face centring end signal, in order to select, in the said portion of the excessive frames of the said video signal corresponding to the face centring, a reduced portion corresponding to a wide or rough centring, of the driver's eyes covering the eyes and their immediate surrounding by applying the anthropometric ratio between the said wide centring and the entire face of a person and means to prepare a wide centring end signal of the eyes, whereas this signal actuates the said means to detect the vertical displacements in the driver's face:

means, operating in parallel with the said means to determine the successive blinking durations and hence actuated by the said eyes centring end signal, in order to determine the time intervals between two successive winks and to trigger a reinforced alarm as soon as these time intervals show an irregularity exceeding a set threshold;

means for continuous update of the data regarding at least one of the following parameters: horizontal displacements, vertical displacements, blinking durations, intervals between successive winks, in order to perfect the approximations of the normal values of the parameter involved for the driver actually present and in awake condition.

Advantageously, the sensor/electronic processing unit assembly is realised as described above and illustrated in both patent applications mentioned previously having same inventor as the present invention.

The object of the invention is also, as a new industrial product, an automotive vehicle rear mirror, characterised in that its mirror consists of a two-way glass and in that it comprises, behind this glass, an optoelectronic sensor which works together with an electronic unit such as described in the French patent application n° 96.09420 made on Jul. 26, 1996 and the international patent application (P.C.T.) PCT/FR97/01354 made on Jul. 22, 1997, whereby this unit is also arranged inside the rear mirror and capable of triggering an alarm device as soon as the said unit determines that the vertical movements of a person's eyelids looking at the front face of the said glass correspond to a blinking duration exceeding a pre-set threshold included in the time interval comprised between the duration a woken person's blinking and that of a person falling asleep.

Preferably, the said rear mirror carries at least one light-emitting diode at least in the infrared range which is actuated at least when the surrounding luminosity becomes insufficient to light the driver's face, whereas the said optoelectronic sensor is sensitive, among other things, to the infrared radiation's transmitted by the said diode.

Advantageously, in the device and the rear mirror of the invention, the sensor, said associated electronic circuitry and said integrated circuit are constitued of an electronic chip arranged inside the casing of the rear mirror.

We shall now describe a preferred embodiment of a device according to the invention, implementing the process of the invention, as well as certain variations of the said, with reference to the appended drawings, on which.

While referring first of all to FIGS. 1 to 6, we shall begin the detailed description of the preferred embodiment according to the invention with that of the optic and mechanic device with the optoelectronic sensor (micro video camera or MOS sensor with integrated lens) and its associated electronic assembly, consisting mainly of one or several chips, which transform the picture received by the sensor into a video signal which is processed in order to detect any sleepiness of the seating driver, as observed by the said sensor.

Indeed, the invention uses mainly the blinking variation of a person hen passing from an awake condition to a dizzy or sleepy condition: a person wake blinks his/her eyelids, hence his/her eyelashes, at relatively regular intervals, approx. every 100 to 200 ms, whereas the duration of this person' blinking when sleepy accelerates to 500 to 800 ms, whereby the blinking intervals increase and vary.

In the video signal from the optoelectronic sensor at 50 or 60 corresponding frames (of same nature) per second, detection takes place every 20 or 16.66 ms respectively, which enables to distinguish easily 100 to 200 ms or 500 to 800 ms durations (5 to 10 frames for awake condition or conversely 25 to 40 frames for sleepy condition in the case of 50 frames of same nature per second) and hence to distinguish the awake condition from the dizzy or sleepy condition of a person.

When using such a distinction in the case of an automotive vehicle driver, it is advisable to better visualise the driver's face, i.e. to direct the input or reception optic axis of the said sensor towards the driver's face. The means provided in the preferred embodiment of the invention consists in taking advantage from the fact that a driver directs the rear mirror of his/her vehicle towards his/her face in order to view the rear of the vehicle by reflection onto the glass of the rear mirror.

Figure 1:
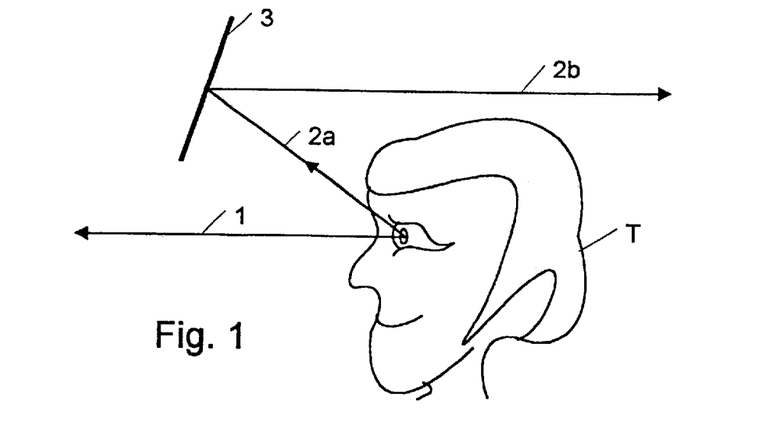
FIGS. 1 and 2 are views, respectively a side view and a top view, illustrating schematically the head of an automotive vehicle driver and his/her front and rear vision axes.
Figure 2:
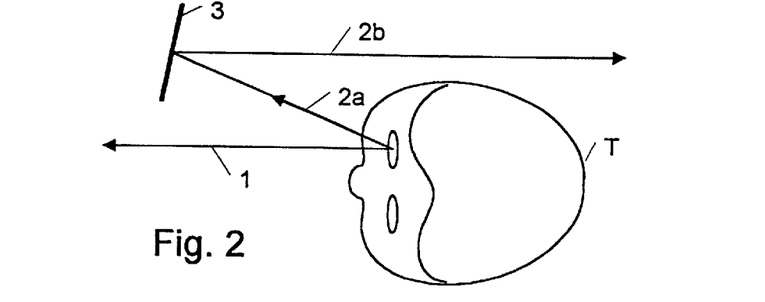
Figure 3:
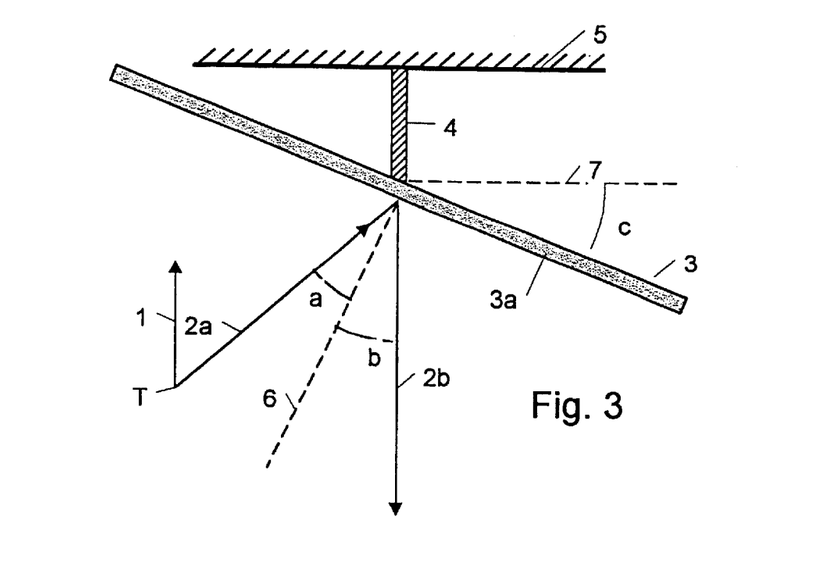
FIG. 3 illustrates schematically the conventional arrangement of an inside rear mirror glass in an automotive vehicle and the different vision axes of the driver, whereas this figure corresponds to the state of the art.

With reference to FIGS. 1 to 3, let us recall the operation of the conventional rear mirrors accommodated inside a vehicle in central position, whereas they are fixed, with the possibility of adjusting the orientation of the glass over a portion of the bodywork inside the vehicle.

Schematic FIGS. 1 and 2 show, laterally and from the top respectively, the head T of a driver who is able to observe the street or road on which his/her vehicle is located, on the one hand, in front of him/her (arrow 1) and, on the other, behind him/her (arrows 2a and 2b) thanks to the mirror 3 of the rear mirror thus suitably oriented. The said arrows 1, 2a, 2b represent the trajectory of the light rays, 2b corresponding to the ray reflected onto the mirror 3.

While considering now schematic FIG. 3, which represents the mirror 3 of the rear mirror, a mirror fixed by an arm 4 on a portion 5 of the bodywork inside the vehicle, with a possibility of orientation, the aiming axes or arrows 1, 2a, 2b of FIGS. 1 and 2 are clearly visible. It can be noted that the axes or arrows 1 and 2b are parallel and directed along the direction of the street or of the road.

FIG. 3 also represents, but as a dotted line, the optic axis 6 perpendicular to the face 3a of the mirror 3 of an inside rear mirror dividing the angle formed by the directions 2a and 2b into two equal halves (angles a and b equal) according to the reflection laws, and the axis 7 perpendicular to the axis 2b and hence parallel to the supporting portion 5, whereas the angle c between the directions 7 and 3a is equal to the angles b and a.

Figure 4:
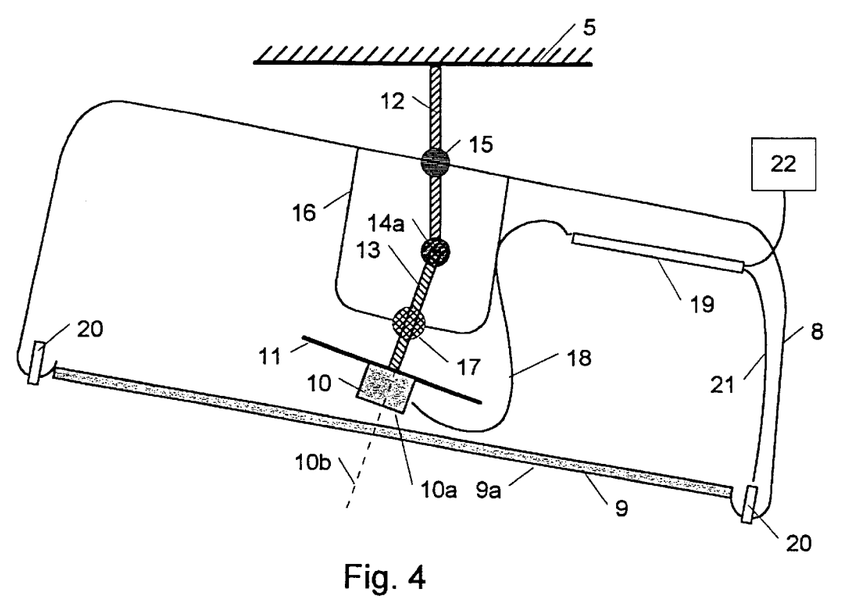
FIGS. 4 and 5 represent respectively the assembly and the articulations of a rear mirror with the optoelectronic sensor and its electronic associated circuitry within the framework of the invention.
Figure 5:
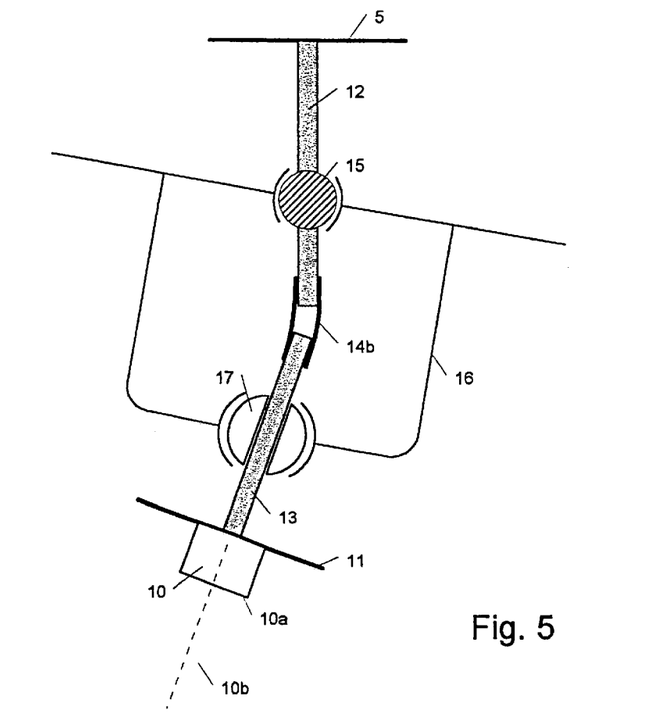

Having mentioned these operating principles of the inside rear mirror, we shall now with reference to FIGS. 4 and 5 expose the mechanic assembly enabling to direct effectively the input optic axis of the optoelectronic sensor towards the seating driver's face, while taking advantage of the fact that the mirror 3 of a rear mirror is oriented by the seated driver, if it was not the case already, so that the driver's aiming axis 2a is directed towards the head T of the driver. Indeed, if the input optic axis of the sensor is indeed directed towards the driver's face, the video signal produced by the said driver will contain the information necessary to determine the blinking duration of the said driver.

First of all within the framework of the preferred embodiment of the invention, the rear mirror 8 comprises, unlike conventional rear mirrors, a two-way mirror 9 (FIG. 4) whose face 3a directed towards the driver plays the same part as the face 3a of the mirror 3 of a conventional rear mirror (FIG. 3), but which enables a sensor 10 (consisting of an electronic microcamera or an MOS sensor with built-in lens), carried by a support 11 (rotating with the two-way mirror 9) to receive at least the picture of the seated driver's face when the two-way mirror 9 (with the rear mirror 8) is suitably oriented by the driver to perceive the street or the road behind him or her or is already so oriented (as it is the case for the conventional mirror 3 of FIG. 3).

The Cardan-type mechanic articulation, illustrated on FIGS. 4 and 5 (the latter figure being a more detailed view of a portion of FIG. 4), enables automatic correct orientation of the support 11, with the sensor 10, by the driver when he/she adjusts his/her rear mirror or when the mirror is already adjusted, and hence the receiving face 10a of the sensor 10 so that it perceives the picture of the seated driver's face, whereby his/her input optic axis 10b is directed towards the seated driver's head because of the angle between the mirror 9 and support 11 of the sensor 10.

To this end, the articulation for the support 11 comprises two rods 12 and 13 which are articulated freely in relation to one another by a trunnion 14a (FIG. 4) or a sleeve 14b (FIG. 5). The rod 12 is fixed to a portion 5 of the bodywork by one of its ends and goes through the casing of the rear mirror 8 thanks to the trunnion 15 (made of a ball and two more or less hemispheric caps) before entering with its other end the sleeve 14b or being fixed to the trunnion 14a, whereas the rod 13 carries rigidly, on one end, the support 11 of the sensor 10 and goes through the yoke 16 of the rear mirror 8 thanks to a hollow trunnion 17 (with a ball through which runs a channel in which the rod 13 enters and rotating inside two more or less hemispheric caps carried by the yoke 16) before joining by its other end the trunnion 14a or the sleeve 14b.

Such an articulation, which maintains permanently an appropriate angle between the mirror 9 and the support 11, enables at the same time the usual orientation of the inside rear mirror by the driver and the orientation of the support 11 of the sensor 10 so that the face 10a of this sensor receives the picture of at least the seated driver's face when the rear mirror is suitably oriented.

The optoelectronic sensor 10 sends through a conductor 18 in an electronic analysis unit 19 (advantageously consisting of a chip casing or chips accommodated inside the rear mirror 8), the video signal prepared on the basis of the picture received on its face 10a.

Light-emitting diodes 20 can be provided in order to transmit, towards the seated driver, when the rear mirror is suitably oriented, an infrared radiation, capable of lighting at least the seated driver's face, when the surrounding light (including that of the dashboard) is insufficient for the correct operation of the sensor 10, which in this case must be sensitive to infrared radiation, and of its electronic unit 19; these diodes can be energised, possibly gradually, and controlled for instance by the electronic unit 19 thanks to a photoelectric cell (not represented) or in response to pixel signals (in the video signal) of insufficient intensity (as represented schematically by the driver 21).

The alarm then actuated when the driver is falling asleep, by the electronic unit 19, is illustrated schematically 22 on FIG. 4, on which the power supplies of the sensor 10, of the electronic 19 and of the diodes 20 have not been represented in order to simplify this figure.

The unit 19 could, as a variation, be arranged outside the rear mirror casing.

We shall now divulge the way the video signal from the optoelectronic sensor 10 is processed in the electronic analysis unit 19 (with an electronic microcamera or an MOS sensor with built-in lens followed by an electronic unit), whereas this video signal comprises a succession of frames (of same nature) corresponding to the rhythm of 50 or 60 such frames per second (either the even or odd-numbered frames in the case of a signal with two interlaced frames per picture, or the single frames in the case of a signal with a single frame per picture); whereas the object of this processing is continuous monitoring of the seated driver's watchfulness while determining, in real time and continuously, the blinking duration of his/her eyes and while triggering, in case when the driver is apparently falling asleep (revealed by the variation of this duration) an alarm signal capable of waking him/her up.

The process and the device, according to the present invention implementing, for locating and circumscribing a moving zone (i.e. successively the driver, his/her face and his/her eyes, in particular his/her eyelids) and for determining the direction and possible the speed of this movement, the process and the device according to the patent applications above mentioned, whose descriptions are integrated into the present description as a reference, it is useful to sum up the process described in these patent applications.

In these applications, the video signal (generated by a video camera or another sensor), which comprises a succession of frames of same nature (consisting of the corresponding frames, either even or odd-numbered, in the case of a video system with two interlaced frames per picture, or the successive frames in the case of a video system with a single frame per picture) is processed in order to, successively     deduct, from the variations in the value or intensity of each pixel between a frame and the corresponding former frame         on the one hand, a binary signal, noted DP, whose both possible values are significant, one of a variation in the pixel value and the other, of a non-variation, values which can be noted for instance <<1>> and <<0>> respectively, and         on the other, a digital signal, noted CO, with a reduced number of possible values, whereby this signal is significant of the magnitude of this variation in the pixel value;

distribute according to a matrix, on a noria basis, values for both these signals DP and CO for the same frame scrolling through the matrix; and     derive, from this matrix distribution, the requested displacement and its parameters (location, direction and speed).

This latter displacement detection operation implements preferably, according to the above patent applications,     the formation of orthogonal histograms along two axes, for example Ox and Oy, of at least the signals DP and CO, distributed as a matrix in the previous operation, and     the location in each histogram relating to DP and CO, of a variation field significant of CO with simultaneously DP =<<1>>.

The present invention performs successively, by implementing the process and device according to the patent applications mentioned above, whose approach has just been summed up:

in a preliminary phase, detecting the presence of a seated driver;

in a first phase, centring the driver's face in the frames of same nature, or corresponding, successive frames of the video signal;

in a second phase, centring the driver's eyes inside the face centring;

in a third phase, determining the successive durations of the driver's winking and possibly determining the time intervals between two successive winks;

in a fourth phase, comparing the blinking durations with a certain threshold, while generating an alarm signal capable of waking up the driver as soon as this comparison shows that the said threshold has been exceeded upwards by the said duration, and possibly the comparison of the variations of the time intervals between two successive winks with another threshold, while generating a reinforced alarm signal as soon as this comparison shows that the latter threshold has been exceeded upwards.

We shall now describe more in detail the embodiment of each of these five phases by the process and the device according to the invention.

The preliminary phase, detecting the presence of a seated driver and launching the first face centring phase, is triggered by a switch actuated manually or otherwise, notably by implementing the process and device of the patent applications mentioned above, it starts effectively by adjusting the rear mirror in order to orient the front face 9a of the two-way mirror 9 of the former (FIG. 4) towards the driver so that he/her can see in this mirror the street or road behind him/her in case when such an adjustment proves necessary.

Figure 6:
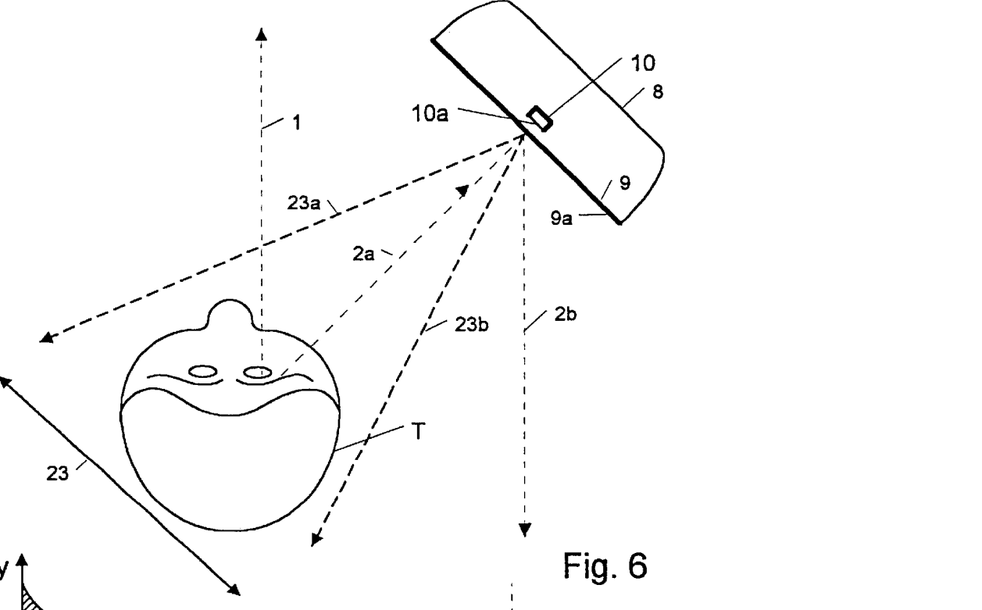
FIG. 6 illustrates the field of the optoelectronic sensor provided in the rear mirror on FIGS. 4 and 5.

FIG. 6 illustrates, between the directions 23a and 23b, the field 23 of the sensor 10, whereas the head T of the driver should be situated, after adjusting the inside rear mirror 8, as described with reference to FIGS. 4 and 5, inside and in the central zone of this conical field 23. This field may be relatively narrow, since the displacements of the driver's head T when driving are limited (except in rare situations); limiting the field improves the sensitivity of the device since the driver's face picture, received by the face 10a of the sensor suitably oriented at the same time as the mirror 9, covers quite an important surface in the frames of the video signal; it is therefore represented by a number of pixels which is a notable fraction of the total number of pixels per frame.

FIG. 6 shows the directions or light rays 1, 2a and 2b of FIG. 3.

The driver's position is advantageously detected by the displacements of his/her head, in particular his/her face, when adopting a driving posture, by implementing the process and the device according to both patent applications mentioned above, which enable detecting displacements, as summed up above.

In fact, the driver's sitting down and the resulting displacement of his/her head T are revealed by the large number of pixels of the video signal for which the binary signal DP has the value <<1>> corresponding to a significant variation of the value of the pixel between two successive corresponding frames and the digital signal CO takes on quite a high value.

The ratio of the number of such pixels (with DP and CO showing the values defined above) to the total number of pixels of a frame, when the driver is sitting down, depends on the size of the sensor's field of vision on either side of the head T of the driver at the steering wheel. If the field of vision is narrow (angle reduced between 23a and 23b, FIG. 6), it can be considered for instance that if more than half the 'moving' pixels of a given frame show a DP and a CO with the values mentioned above, the driver is sitting down. A 50% threshold can then be considered between the number of 'moving' pixels and the total number of pixels in a frame and in such a case, the preliminary phase ends with the generation, when this threshold is exceeded upwards, of a flag <<1>> signalling the driver's presence, launching the next processing phase of the video signal, while starting with the first phase. Obviously, the threshold adopted for triggering the flag <<1>> can differ from 50% while taking into account the field of vision of the sensor 10.

As a variation, the flag <<1>> signalling the driver's presence and launching the first phase can be generated by a command outside the electronic unit 19, but triggering the latter, for instance caused by the actuation of the ignition key, buckling the driver's safety belt or the driver's seat sagging under his/her weight.

When the driver's presence has been signalled and the presence flag <<1>> generated, the first processing phase of the video signal can begin. It consists, as indicated previously, in centring the driver's face within the video signal while trimming out any superfluous portions, above, below and on either side of the head, in the picture received by the detector 10.

To this end, by implementing the process and the device according to the invention, these are the horizontal displacements, i.e. from right to left and vice versa, which are detected, since a driver's head has a tendency to move horizontally rather than vertically, i.e. looking up and down.

Therefore, a horizontal displacement signal is extracted from the flow of data represented in the corresponding successive frames of the video signal, relating to the position, the direction and possibly the speed, using the running matrix of the values DP and CO and an analysis is performed by selecting along two privileged co-ordinate axes, for example the conventional axes Ox and Oy of Cartesian co-ordinates, by implementing histogram formation means according to the patent applications mentioned above.

Counting, at the end of the frames, the pixels which are significant of a horizontal displacement enables to detect displacement peaks along the face edges, for which the luminosity variations, hence the pixel value variations, are the most salient, as well in horizontal projection along Ox as in vertical projection along Oy for example.

Figure 7:
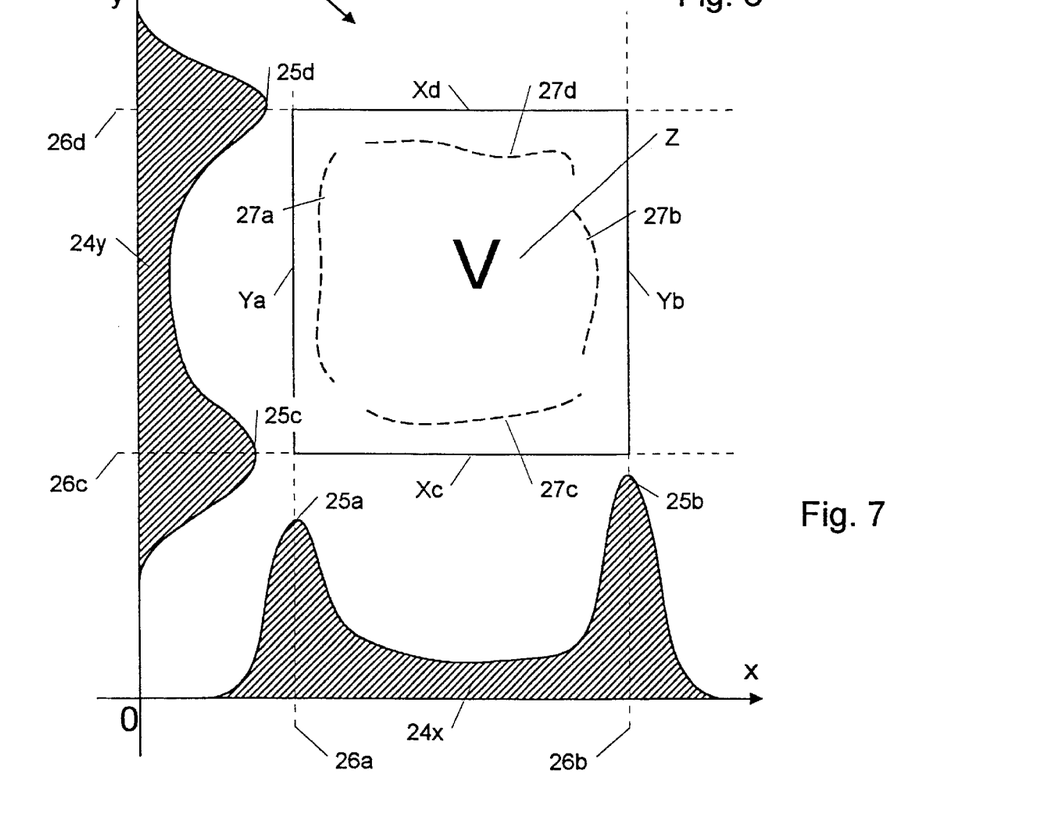
FIGS. 7 and 8 represent the way of centring the driver's face when seated.

This is illustrated on FIG. 7 on which the axes Ox and Oy have been represented, as well as the histograms 24x, along Ox, and 24y, along Oy, i.e. in horizontal and vertical projection respectively.

The peaks 25a and 25b of the histogram 24x, and 25c and 25d of the histogram 24y, delineate by their respective co-ordinates 26a, 26b, 26c, 26d, a frame limited by the segments Ya, Yb, Xc, Xd enclosing the face V of the driver, surrounded by the respective undulations 27a, 27b, 27c, 27d which illustrate the slight movements of the driver in zones where the intensities of pixels vary more significantly during the said movements.

Figure 8:
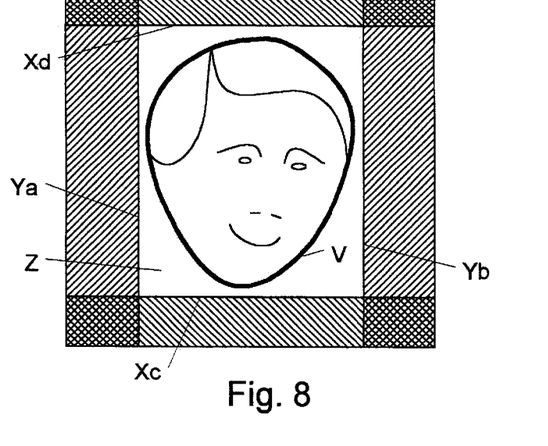

Locating the co-ordinates 26a, 26b, 26c and 26d corresponding to four peaks 25a, 25b, 25c and 25d of both histograms 24x and 24y, therefore enables to better define and frame the position of the driver's face V in the zone Z and suppress, for the next processing phases of the video signal, the upper, lower, right and left portions in relation to the frame Xc, Xd, Ya, Yb, as illustrated on FIG. 8 by hatched zones surrounding the face V, which enables to enhance the resolution and possible the speed of the analysis bearing upon the central zone Z, not hatched, surrounded by the segments Xc, Xd, Ya, Yb and containing the face V.

This operation consisting in framing the entire face is renewed at regular intervals, for instance every ten frames of the video signal, and the mean values (in the course of time) of the co-ordinates 26a, 26b, 26c, 26d are determined while redefining the frame, which is slightly variable, but relatively stable, Xc, Xd, Ya, Yb around the face V. It appears therefore that the position of the said frame (with the zone delineated for later analysis) is rather robust, i.e. stable over the course of time.

A new framed face flag <<1>> is generated after establishing the framing of the driver's face V.

Generating this flag triggers the second phase, which consists in reducing the processing frame further, i.e. the frame of the driver's eyes.

This second phase comprises, preferably, a preliminary operation consisting in using, in the electronic unit 19, the usual anthropometric ratio between the eye zone and the whole face of a human being, notably in the vertical direction, whereas the eye zone occupies only a limited portion of the whole face.

Figure 9:
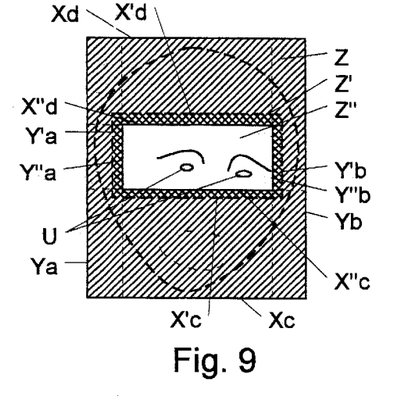
FIGS. 9 and 10 represent the way of centring the driver's eyes when seated.

The electronic unit 19 determines then, in this preliminary operation, by ratio a more limited frame Z', including the eyes U of the driver, in the previous frame Z of the face V, limited by Ya, Yb, Xc, Xd, whereas this frame Z' is delineated, as illustrated on FIG. 9, by the segments Y'a, Y'b, X'c and X'd inside the frame Ya, Yb, Xc, Xd (zone Z).

Thus, the external hatched zones (simple hatches) are then suppressed on FIG. 9 in order to keep the frame Z' solely, which facilitates final framing of the eyes in the second phase and increases its accuracy and the speed of its determination.

Upon completion of this preliminary operation, if any, which generates a rough eyes framing flag <<1>>, or directly after the first processing phase, i.e. respectively in response to the apparition of the rough eyes framing flag <<1>> or of the framed face flag <<1>> respectively, the electronic unit 19 carries out the second effective framing phase while zeroing in on the driver's eyes and detecting in the matrix of the DP and CO, the pixel locations for which DP=1 and CO exhibits a high value, notably for displacements in the vertical direction since the eyelids wink up and down.

When the number of such pixel locations reaches a certain threshold in the frame Y'a, Y'b, X'c, X'd (zone Z) in case when the preliminary operation is provided or in the frame Ya, Yb, Xc, Xd (zone Z) failing such a preliminary operation, whereas this threshold corresponds for instance to 20% in relation to the total number of pixels in the frame Y'a, Y'b, X'c, X'd in the former case and to 10% in relation to the total number of pixels in the frame Ya, Yb, Xc, Xd in the latter case, a fine eyes framing flag <<1>> is generated; this flag indicates in fact that the driver's eyelids are active, since it is caused by the driver's blinking; movements in the vertical direction detected in the same manner as the horizontal displacements of the driver's face in the first phase.

Figure 10:
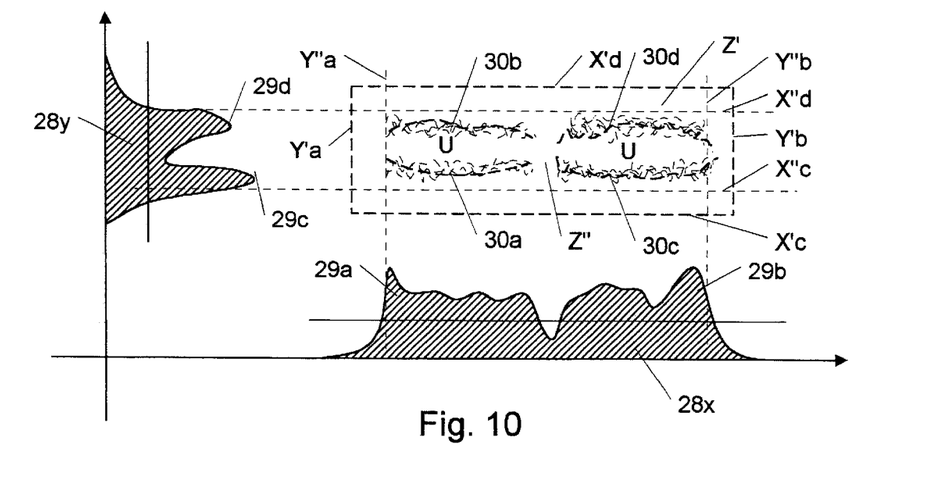

FIG. 10 illustrates the possible frame Y'a, Y'b, X'c, X'd delineating the rough framing zone Z' of the driver's eyes, as well as the histograms 28x along the axis Ox and 28y along the axis Oy of the vertical displacements of the driver's eyelids, i.e. pixels of the matrix showing, by their DP and their CO, such displacements. These histograms 28x and 28y, corresponding to histograms 24x and 24y of the horizontal displacements of the driver's face, illustrated on FIG. 7, determine by their peaks 29a, 29b, 29c, 29d, horizontal segments X"c and X"d and vertical segments Y"a and Y"b delineating, inside the zone Z'; a zone Z" enclosing the driver's eyes whose edge displacements are specified at 30a and 30b for one eye and 30c and 30d for the other eye.

The position of the frame Y"a, Y"b, X"c, X"d is updated by determining the mean values in the course of time, for instance every ten frames, coordinates of the peaks 29a, 29b, 29c, 29d and on the basis of the generation of the fine framing eyes flag <<a1>>, these are only the pixels enclosed in the frame delineated of the zone Z" which are processed in the third phase triggered by this flag (the zone Z" is illustrated in white on FIG. 9).

In this third phase, the durations of eyes blinking are determined, and possibly the time intervals between two successive winks, while perfecting the analysis of the vertical displacements of the eyelids in the zone Z" by processing, in the electronic unit 19, portions of the successive frames of the video signal corresponding to this zone Z", which enables a great accuracy.

Figure 11:
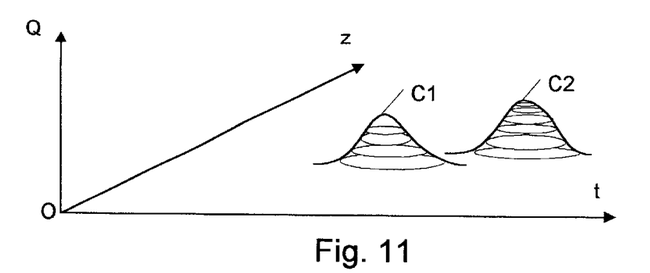
FIGS. 11 and 12 are related to the measurement of the driver's blinking duration and to the time intervals between two successive winks.

FIG. 11 illustrates in a system of co-ordinates along three orthogonal directions, i.e. the direction OQ carrying CO, hence the pixel variation intensities, corresponding to the vertical movement of the eyelids, Ot which carries the time intervals between two successive winks and Oz which carries the blinking durations, hence three different parameters enabling to determine the transition from awake condition to the driver's sleepy condition. Two successive winks C1 and C2 are represented on FIG. 11.

Figure 12:
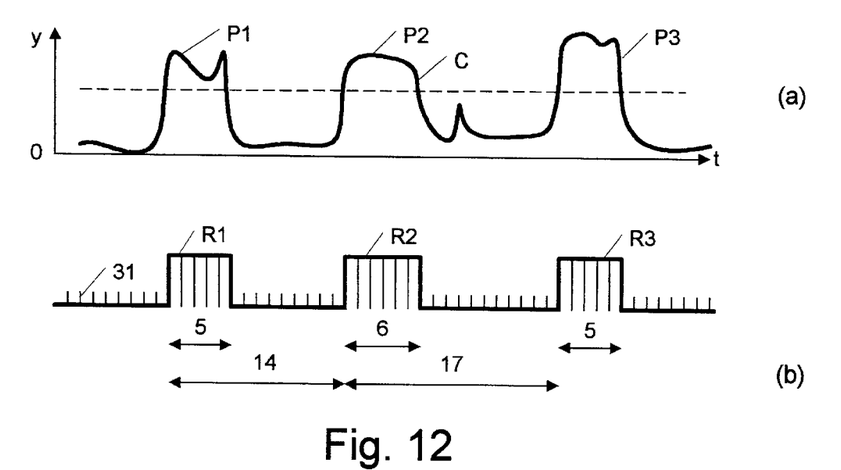

FIG. 12 illustrates with the curve C, on the portion (a), the time variation along Ot of the number of pixels per frame in significant vertical movement (for which DP=1 and Co has quite a large value), the successive peaks P1, P2, P3 of the number of moving pixels corresponding to winks.

The successive corresponding frames relating to the curve C are represented schematically and partially, on the portion (b) of FIG. 12, by vertical lines, such as 31, whose peaks P1, P2, P3 are enclosed with rectangles R1, R2, R3 respectively, whereas both portions (a) and (b) of FIG. 12 have been arranged one below another, synchronously. Finally, FIG. 12 represents the blinking durations (5, 6, 5) and the time intervals (14, 17) between successive winks, in frame numbers, values which correspond to the driver's awake condition.

The electronic unit 19, in this third phase, calculates the successive blinking durations and the successive time intervals between two successive winks and performs a two-dimensional statistical analysis between the successive blinking durations and the blinking intervals. It determines whether the blinking durations exceed a certain threshold, for instance 350 ms, and in this case, trigger an exceeded blinking threshold flag <<1>> and possibly whether the time intervals between two successive winks are relatively constant or conversely significantly variable over the time and in the second case trigger a flag <<1>> indicating intervals between variable winks.

The first flag is used to trigger an alarm, a sound alarm for instance, capable of waking up the driver, while the second flag reinforces the alarm, for instance while increasing the sound level.

Figure 13:
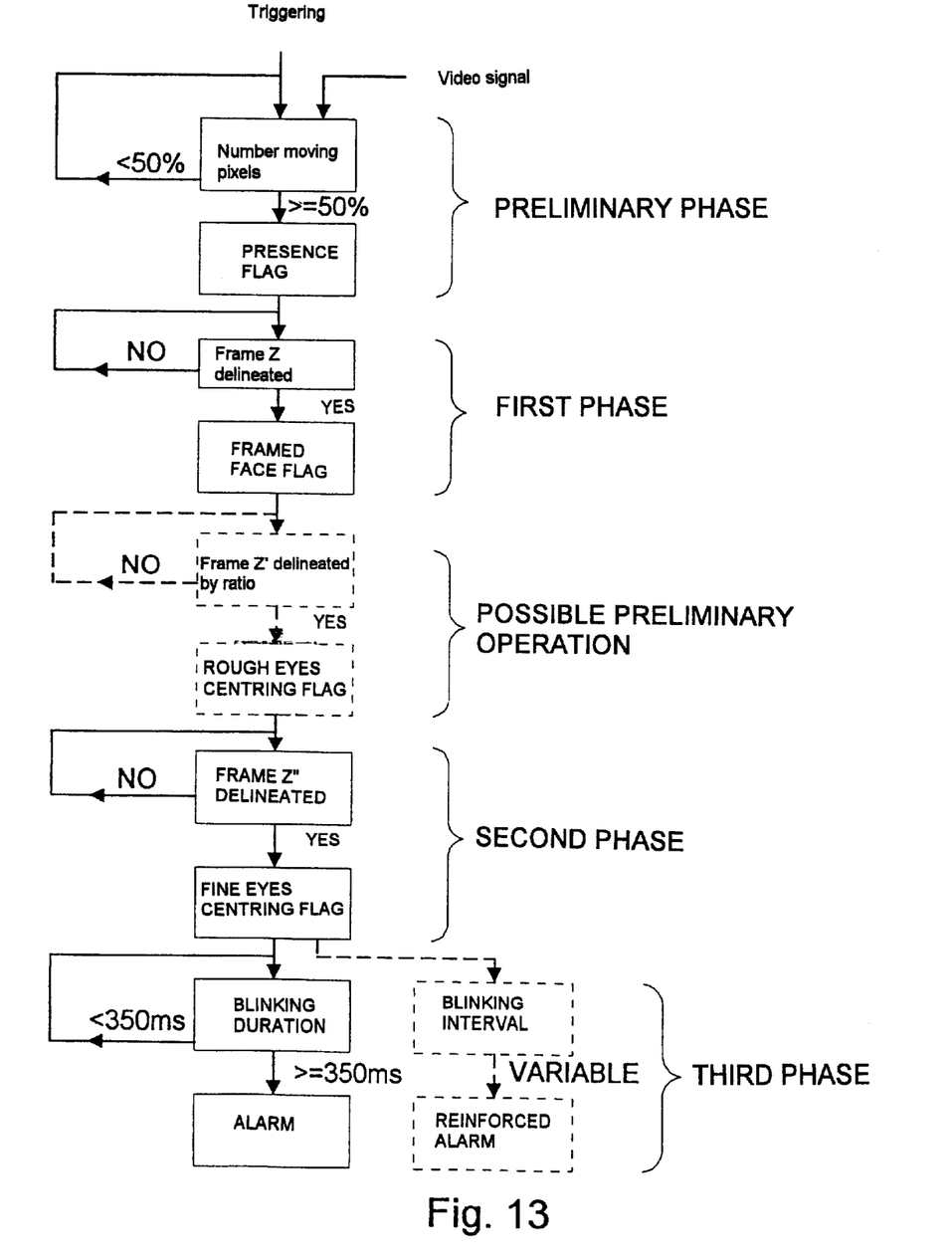
FIG. 13 represents the flowchart of the successive operating phases.

The flowchart appended as a tracing board 6 (FIG. 13) sums up the various successive phases.

Dialogue with the outside is carried out preferably in series mode (CAN-VAN).

The whole transducer, associated electronic circuitry and the processor or calculator, may be advantageously integrated in an electronic chip housed in the interior rear mirror of the vehicle.

The rear mirror of FIGS. 4 and 5 suits a driver seated on the right seat as well as the left seat, for right-hand driving countries, and may also be an external rear mirror, notably on the driver's side.

It is particularly interesting to use a MOS type sensor, which permits a determination of the value of a pixel, location by location of pixel, without being obliged, as with a CCD sensor, to extract pixels values line by line and location by location in each line.

Figure 14:
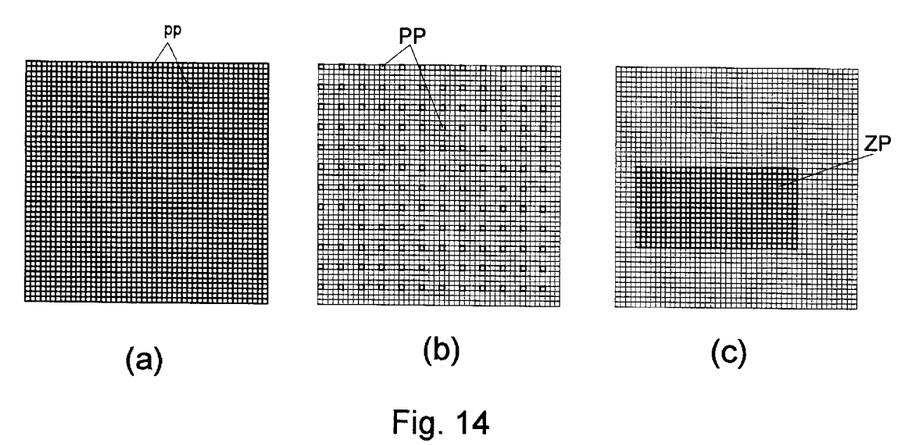
FIG. 14 represents advantages of an embodiment having as a sensor, a MOS type sensor.

As represented FIG. 14, it is then possible to realise a variable selection of the pixels positions: instead of (a) examining all the positions pp of pixels on the whole image (large amount of treatments), one may (b) examine only specific meshed pixels PP making a regular network representing the overall image of the driver's face and his immediate environment (zoom effect); finally one may (c) select a specific area ZP, the eyes one by treating only the pixels of that area (constant power of treatment).

Figure 15:
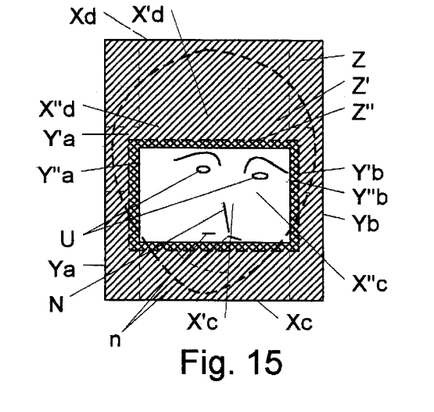
FIG. 15, lastly, is a variation of FIG. 9, the privileged observation area including the nose, in addition to the eyes.

On FIG. 15, which is a variation of FIG. 9, having the same references, one has foreseen for the final phase of the driver supervision, not only the eyes area (as in the case of FIG. 9), but also the nostrils n of the nose N, the observation of the displacements of the outline or dark spot of nostrils allows improvement of the steadiness of the observation area including the eyes.

It goes without saying that the invention is not limited to the preferred embodiment described and illustrated, nor to its variations mentioned above; conversely the invention covers the modifications, variations and improvements falling into the category of the invention definitions given in the preamble and the appended claims.

What is claimed is:

1. A process for continuous monitoring of the driver's watchfulness in an automotive vehicle, in order to detect and to prevent any possible sleepiness of the former, comprising:
   producing a video signal, significant in real time of the successive pictures of at least the driver's face;
   processing this signal, successively and continuously, to
      detect in this signal the portion corresponding effectively to the image of the driver's head,
      determine the value of a parameter in relation to the blinking of the eyelids, with a notable modification when the driver passes from the awake condition to the sleepy condition, on either side of a threshold, and
      locate in real time when the value of this parameter exceeds this significant threshold of the driver's transition from awake condition to sleepy condition; and triggering, in response to the threshold being exceeded, an alarm capable of waking up the driver;

and which is characterised in that the video signal is produced by using an optoelectronic sensor interconnected with a rear-mirror on the automotive vehicle, dimensioned and arranged to essentially receive the driver's face image when seated and whose optic axis for receiving the light rays is directed towards the driver's head when the rear-mirror is oriented correctly; and processing the said video signal, includes after detecting the presence of the driver on his/her seat, successively and continuously, detecting, from an analysis of moving pixels between two successive frames of same nature of said video signal, the horizontal movements of the driver, in order to centre the face of the said driver within the successive corresponding frames of the video signal, detecting, from an analysis of moving pixels between two successive frames of same nature of said video signal, the vertical movements in the face, thus centred, of the driver in order to centre his/her eyes, determining, from an analysis of moving pixels between two successive frames of same nature of said video signal, the successive blinking durations of the eyes, thus centred, of the driver, whereby the said durations make up the said parameter, comparing these successive blinking durations, thus determined, with a threshold significant of the transition from awake condition to sleepy condition of the driver, and triggering, when the blinking durations exceed the said threshold upwards, an alarm capable of waking up the driver.

2. A process according to claim 1, characterised in that the said sensor is placed in the casing of the rear mirror behind the mirror of the former which consists of a two-way mirror, the reception optic axis (2a) of said sensor being symmetrical to an axis (2b) oriented in the vertical median plane of said vehicle, related to an orthogonal axis (6) to said two-way mirror.

3. A process according to claim 1, characterised in that the presence of the driver on his/her seat is detected while determining the number of pixels corresponding in the successive frames of the same nature in the video signal for which a significant movement is detected and by comparing this number with the total number of pixels per frame of the video signal, in order to determine whether the ratio between the number of pixels representing a displacement and the total number of pixels per frame exceeds a threshold significant of the transition from the driver's absence on his/her seat to the presence of a driver in his/her seat.

4. A process according to claim 1, characterised in that, between the detection phases of horizontal displacements, in order to centre the driver's face, and the detection of vertical displacements, in order to frame the driver's eyes, a wide centring phase of the eyes has been provided while being limited to a portion of the centred face, covering the eyes and their immediate surrounding, by applying the anthropometric ratio between the said portion and the entire face of a person.

5. A process according to claim 1, characterised in that simultaneously to the determination phase of the blinking durations, a determination phase of time intervals between two successive winks has been provided and a reinforced alarm should be triggered as soon as those time intervals present an irregularity which exceeds a set threshold.

6. A process according to claim 1, characterised in that continuous update of the data is performed, regarding at least one of the following parameters: horizontal displacements, vertical displacements, blinking durations, intervals between successive winks, in order to perfect the approximations of the normal values of these parameters for the driver actually present and in awake condition.

7. A process according to claim 1, characterised in that the different successive phases of the process are performed using successive computer programmes which would process successive values of the corresponding pixels of the frames of same nature in the video signal obtained from the said sensor.

8. A device for continuous monitoring of the driver's watchfulness in an automotive vehicle, in order to detect and to prevent any possible sleepiness of the former, implementing the process according to claim 1 and which is characterised in that it comprises, in combination:

a) an optoelectronic sensor (10) which, in combination with associated electronic circuitry (19), prepares, in response to the reception of light rays, a video signal with frames of the same nature, or corresponding, successive frames, whereas the said sensor is interconnected with a vehicle rear mirror (8) and dimensioned and arranged to essentially receive the driver's face image when seated and whose optic axis (10b) for receiving the light rays is directed towards the driver's head (T) when the rear mirror is suitably oriented; and b) at least an integrated circuit including means to detect the driver's presence on his/her seat in the vehicle, and to prepare a presence signal;

means, actuated by this presence signal, to detect on the basis of an analysis of moving pixels between two successive frames of same nature of said video signal, the horizontal displacements of the said driver, in order to centre his/her face (V) in the successive frames of same nature in the said video signal and to prepare a signal at the end of the face centring;

means, actuated by the said end signal of the face centring, to detect on the basis of an analysis of moving pixels between two successive frames of same nature of the portion of the successive frames of same nature in the said video signal corresponding to the face centring, the vertical displacements in the face, thus centred, of the driver, in order to centre the eyes (U) of the said driver, within the said portion of the frames of this signal and to prepare a face centring end signal of the driver's eyes;

means, actuated by the said eyes centring end signal, to determine on the basis of an analysis of moving pixels between two successive frames of same nature of the portion of the successive frames of same nature in the said video signal corresponding to the eyes centring, the successive durations of the driver's blinking;

means to compare these successive blinking durations, thus determined, with a threshold significant of the transition from awake condition to sleepy condition of the driver; and means to trigger, when the blinking durations exceed the said threshold, an alarm (22) capable of waking up the driver.

9. A device according to claim 8, characterised in that the said sensor (10) is placed in the casing of the rear mirror (8) behind the mirror of the former which consists of a two-way mirror (9), said sensor being carried by a first extremity of a first rod (13) crossing, through a trunnion (17), a clamp carried by the rear mirror casing (8), inside of it, the second extremity of this rod (13) being freely articulated, with a seam (14*a*, 14*b*), to the first extremity of a second rod (12) crossing, through a trunnion (15), the rear mirror casing (8), while the second extremity of said second rod (12) is fixed to the bodywork of the vehicle (in 5) above the front wind-screen, in order that the reception optic axis (2*a*) of said sensor being symmetrical to an axis (2*b*) oriented in the vertical median plane of said vehicle, related to an orthogonal axis (6) to said two-way mirror.

10. A device according to claim 8, characterised in that the said means to detect the presence of the driver on his/her seat and to prepare a presence signal consist of means to determine the number of pixels in the successive frames of the same nature in the said video signal for which a significant movement is detected, means to compare this number with the total number of pixels per frame in the video signal, in order to determine whether the ratio between the number of pixels representing a displacement and the total number of pixels per frame exceeds a threshold significant of the transition from the driver's absence on his/her seat to the presence of a driver in his/her seat.

11. A device according to claim 8, characterised in that it comprises moreover, means, actuated by the said face centring end signal, in order to select, in the said portion of the excessive frames of the said video signal corresponding to the face centring, a reduced portion corresponding to a wide or rough centring, of the driver's eyes covering the eyes and their immediate surrounding by applying the anthropometric ratio between the said wide centring and the entire face of a person and means to prepare a wide centring end signal of the eyes, whereas this signal actuates the said means to detect the vertical displacements in the driver's face.

12. A device according to claim 8, characterised in that it comprises means, operating in parallel with the said means to determine the successive blinking durations and hence actuated by the said eyes centring end signal, in order to determine the time intervals between two successive winks and to trigger a reinforced alarm as soon as these time intervals show an irregularity exceeding a set threshold.

13. A device according to claim 8, characterised in that it comprises means for continuous update of the data regarding at least one of the following parameters: horizontal displacements, vertical displacements, blinking durations, intervals between successive winks, in order to perfect the approximations of the normal values of the parameter involved for the driver actually present and in awake condition.

14. A device according to claim 8, characterised in that the optoelectronic sensor (10)—electronic unit (19) assembly produces a video signal comprising a succession of corresponding frames of same nature with a succession of lines made of a succession of pixels and processes the said video signal in order to successively deduct, from the variations in the value or intensity of each pixel between a frame and the corresponding former frame
on the one hand, a binary signal, noted DP, whose both possible values are significant, one of a variation in the pixel value and the other, of a non-variation of the pixel value and on the other, a digital signal, noted CO, with a reduced number of possible values, whereby this signal is significant of the magnitude of this variation in the pixel value;

distribute according to a matrix, on a noria basis, values for both these signals DP and CO for the same frame scrolling through the matrix; and derive, from this matrix distribution, the requested displacement and its location and direction parameters.

15. A device according to claim 8, characterised in that said sensor (10), said associated electronic circuitry (19) and said integrated circuit are constituted by an electronic chip arranged in the rear mirror casing (8).

16. A rear mirror for automotive vehicle, characterised in that its mirror consists of a two-way mirror (9) and in that it comprises, behind this two-way mirror, a sensor fitted with optoelectronic circuitry (10) working together with an electronic unit (19) also provided inside the rear mirror and in that the optoelectronic sensor (10)—electronic unit (19) assembly produces a video signal comprising a succession of corresponding frames of same nature with a succession of lines made of a succession of pixels and processes the said video signal in order to successively deduct, from the variations in the value or intensity of each pixel between a frame and the corresponding former frame
a binary signal, noted DP, whose both possible values are significant, one of a variation in the pixel value and the other, of a non-variation of the pixel value, and
a digital signal, noted CO, with a reduced number of possible values, whereby this signal is significant of the magnitude of this variation in the pixel value;

distribute according to a matrix, on a noria basis, values for both these signals DP and CO for the same frame scrolling through the matrix; and derive, from this matrix distribution, the requested displacement and its location and direction parameters: and trigger an alarm device (22) as soon as the said unit determines that the vertical movements of a person's eyelids looking at the front face (9*a*) of the said mirror correspond to a blinking duration exceeding a pre-set threshold included in the time interval comprised between the duration a woken person's blinking and that of a person falling asleep.

17. A rear mirror for automotive vehicle according to claim 16, characterised in that said sensor (10), said associated electronic circuitry (19) and said integrated circuit are constituted by an electronic chip arranged in the rear mirror casing (8).

18. A rear mirror for automotive vehicle according to claim 16, characterised in that it carries moreover at least one light-emitting diode (20) at least in the infrared range which is actuated at least when the surrounding luminosity becomes insufficient to light the driver's face and in that the said optoelectronic sensor (10) is sensitive, among other things, to the infrared radiations transmitted by the said diode.

* * * * *

UNITED STATES PATENT AND TRADEMARK OFFICE
CERTIFICATE OF CORRECTION

PATENT NO.     : 6,304,187 B1
DATED          : October 16, 2001
INVENTOR(S)    : Pirim It is certified that error appears in the above-identified patent and that said Letters Patent is hereby corrected as shown below:

<u>Title page,</u>
Please correct Item [22], "PCT Filed: Jul. 22, 1999" to -- PCT Filed: Jan. 14, 1999 --.

Signed and Sealed this

Tenth Day of September, 2002

Attest:

JAMES E. ROGAN
Attesting Officer      Director of the United States Patent and Trademark Office